US00PP09111P

United States Patent [19]

Drewlow

[11] Patent Number: Plant 9,111

[45] Date of Patent: Apr. 18, 1995

[54] KALANCHOE PLANT NAMED LEGACY

[75] Inventor: Lyndon W. Drewlow, Ashtabula, Ohio

[73] Assignee: Mikkelsens, Inc., Ashtabula, Ohio

[21] Appl. No.: 234,561

[22] Filed: Apr. 28, 1994

[51] Int. Cl.[6] ..... A01H 5/00
[52] U.S. Cl. ..... Plt./87.15
[58] Field of Search ..... Plt. 87.15

*Primary Examiner*—James R. Feyrer
*Attorney, Agent, or Firm*—Foley & Lardner

[57] ABSTRACT

A new and distinct cultivar of Kalanchoe plant named Legacy, characterized by its vivid red-purple flower color, relatively short, broad leaves, good branch branching, early flowering, very floriferous habit, relatively large total inflorescence, and excellent keeping quality.

1 Drawing Sheet

The present invention relates to a new and distinctive cultivar of Kalanchoe plant, botanically known as *Kalanchoe blossfeldiana,* and known by the cultivar name Legacy. Legacy was developed by the inventor through controlled breeding by crossing Mikkelsen Seedling No. 89-307-7 (seed parent) with Mikkelsen Seedling No. 88-537-2 (pollen parent). The new cultivar was selected from the progeny of the stated cross.

Asexual reproduction by stem cuttings in Ashtabula, Ohio has shown that the unique features of this new Kalanchoe are stabilized and are reproduced true to type in successive propagations.

The following characteristics distinguish the new Kalanchoe from both its parent varieties and other cultivated Kalanchoes of this type known and used in the floriculture industry, including comparison cultivar Fascination, disclosed in U.S. Plant Pat. No. 5,889. Color references are to the Royal Horticultural Society Colour Chart.

1. The flower color of Legacy is red purple (71C to 71D), with the flowers of Fascination being a lighter red purple (67B) in color.

2. Legacy has a shorter, broader leaf at 9 to 10 cm long and 6 to 7 cm wide than the leaves of Fascination which are 11 cm long and 6 cm wide.

3. Both Legacy and Fascination have good basal branching. However, Fascination may have lateral branches that remain vegetative after a six-week short day period to induce flowering, especially when grown under long days after the short day treatment. All lateral branches on Legacy are reproductive after short day treatment.

4. Total inflorescence of Legacy is 20 to 22 cm in diameter while Fascination has a much smaller inflorescence diameter of 14 to 16 cm.

5. Leaves tend to be at right angles to the stem on Legacy, while on Fascination the leaves are at 45° angles and tend to hang downwardly thereby making the plant look like it is wilting. The leaves of Legacy protrude straight out from the plant.

6. Legacy is 5 to 7 days earlier to bloom under winter growing conditions, compared to Fascination, while both are similar in bloom time under summer growing conditions.

7. Legacy is a slightly more compact grower than Fascination, averaging 2 to 4 cm shorter under similar growing conditions.

8. Legacy has better keeping quality than Fascination, with flowers keeping up to a week longer on plants of similar flower maturity.

9. Because more of the basal lateral branches set flower buds on Legacy, the total number of flowers on a Legacy plant is greater than on a Fascination plant.

10. Legacy is very adaptable in production and is an excellent performer for production in 10 and 15 cm pots.

The accompanying colored photograph illustrates the overall appearance of this cultivar taken as a face view of the plant and showing the colors as true as it is reasonably possible to obtain in a colored reproduction of this type. The photograph was taken on Dec. 20, 1993 under natural light on an overcast day under a fiberglass greenhouse covering at Ashtabule, Ohio.

The following is a detailed description of my new cultivar, based on plants produced in greenhouses in Ashtabula, Ohio during the winter season of the year. Plants were grown in 10 cm pots and measurements were taken 14 weeks after rooted cuttings wer planted. Height measurements were taken from the soil line of the container. The plants were grown at 65°-68° F. night temperatures under 3500 to 4000 foot candles of light, and 250 ppm nitrogen, 75 ppm potassium, and 250 ppm phosphorous nutritional levels with trace elements added. Habit of growth, plant height, flowering time, size of leaves and peduncle length are influenced by nutritional and environmental conditions, without, however, any variation in genotype.

Color references are made to the Royal Horticultural Society Colour Chart except where general terms of ordinary dictionary significance are used.

Parentage: A controlled cross between female parent Mikkelsen Seedling No. 89-307-7 and male parent Mikkelsen Seedling No. 88-537-2.

Propagation:

*Type cutting.*—Stem tip cutting up to 3 cm long.

*Time to root.*—10 days at 21° C. summer, and 14 days at 21° C. winter.

*Rooting habit.*—Fibrous, fine, abundant.

PLANT DESCRIPTION

Habit and form of growth: Compact, semi-mounded to upright flower clusters above foliage; excellent branching. Environment and use of growth regulators will play a role in final height.

Foliage description: Leaves simple and opposite.

*Size.*—Average, full grown leaves on a plant when grown in a 10 cm pot are 9 to 10 cm long and 6 to 7 cm wide.

*Shape.*—Ovate, apex obtuse, base acute to rounded.

*Texture.*—Glabrous, coriaceous and succulent.

*Margin.*—Crenate, shallow lobed.

*Color.*—Young foliage, top size 146A, underside 146B; Mature foliage, top side 147A, underside 146A.

FLOWER DESCRIPTION

Flowering habits: Inflorescence is a cyme. Terminal flower on main axis opens first, followed by the terminal flowers of the side branches, continuing with the subsequent development of branches in the inflorescence. Inflorescence is made up of the main stem and up to 8 or more lateral branches.

Natural flowering season: Early January. Flowering time under controlled daylength at 20° C. in summer is 10 weeks, in winter 11½ weeks. Flowering time depends on temperature, light intensity and other growing conditions.

Flower bud: Oblong, up to 6 mm long before showing color; developing tubular as flower petals mature; sheathed in 4 yellow green sepals.

Flowers borne: On compound dichasial cymes Primary peduncle 4 mm in diameter just below the first branch of the inflorescence; length will vary depending on growing conditions. Pedicels vary in length depending on where they are in the inflorescence.

Quantity of flowers: Numerous flowers as the main stem plus eight or more lateral branches will have 50 plus flowers each.

Petals:

*Shape.*—Almost rounded, top cuspidate.

*Color.*—Top side when opening red purple 71C to 71D, fading to 72C; underside 72D.

*Number of petals.*—Four (4).

*Size.*—Individual petals 5 mm wide and 6 mm long; flower 14 mm in diameter.

Reproductive organs:

*Stamens.*—Eight (8) in number. Anther shape: Flat elliptical, color yellow-green. Filament color: Yellow-green. Pollen color: Yellow.

*Pistels.*—Stigma shape: Flat, mature color white. Style color: Light green. Ovaries: Four (4) in number, size 5 mm, color green.

Disease resistance: Legacy has shown resistance to powdery mildew. No other disease problems noted to date.

Other important characteristics: Legacy is an addition to a series of Kalanchoes (Majestic, U.S. Plant Pat. No. 7,794, Splendor, U.S. Plant Pat. No. 7,792, Revelry, U.S. Plant Pat. No. 7,795, Keepsake, U.S. Plant Pat. No. 7,798, and Heirloom, U.S. Plant Pat. 7,810) that are matched closely for flowering time, height, branching and growth regulator response. This allows the greenhouse grower to sell all 6 colors at the same time from a single planting date and use the same growing methods on each to end up with a uniform crop. The end result is an easier crop for the grower to produce and a high quality crop for the consumer to buy.

I claim:

1. A new and distanct cultivar of Kalanchoe plant named Legacy, as illustrated and described.

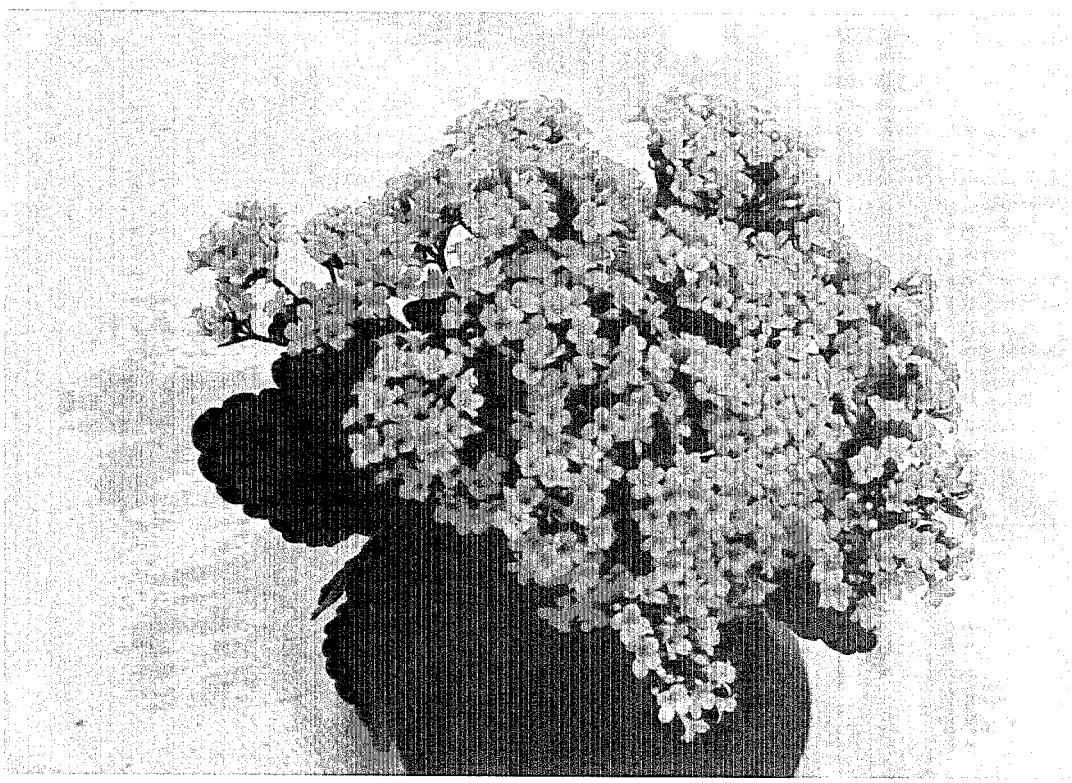

* * * * *